(12) United States Patent
Lohn

(10) Patent No.: US 7,585,467 B2
(45) Date of Patent: Sep. 8, 2009

(54) PIPETTE TIP

(75) Inventor: Jurgen Lohn, Klein Meckelsen (DE)

(73) Assignee: Eppendorf AG, Hamburg (DE)

( * ) Notice: Subject to any disclaimer, the term of this patent is extended or adjusted under 35 U.S.C. 154(b) by 631 days.

(21) Appl. No.: 10/946,708

(22) Filed: Sep. 22, 2004

(65) Prior Publication Data
US 2005/0069460 A1 Mar. 31, 2005

(30) Foreign Application Priority Data
Sep. 30, 2003 (DE) .............................. 103 45 324

(51) Int. Cl.
*B01L 3/02* (2006.01)
(52) U.S. Cl. .................. 422/100; 422/922; 422/931
(58) Field of Classification Search .............. 422/100, 422/922, 931
See application file for complete search history.

(56) References Cited

U.S. PATENT DOCUMENTS 4,072,330 A * 2/1978 Brysch ................. 73/864.14
4,707,337 A 11/1987 Jeffs et al. .................. 422/101
6,197,259 B1 * 3/2001 Kelly et al. ................ 422/100
D465,844 S * 11/2002 Anderson et al. .......... D24/130

FOREIGN PATENT DOCUMENTS

| DE | 25 26 296 | 12/1976 |
| DE | 199 05 027 | 8/2000 |
| DE | 299 14 295 | 1/2001 |
| EP | 0 733 404 | 9/1996 |
| EP | 0 743 095 | 11/1996 |

* cited by examiner

*Primary Examiner*—Walter D Griffin
*Assistant Examiner*—Lessanework Seifu
(74) *Attorney, Agent, or Firm*—Vidas, Arrett & Steinkraus, P.A.

(57) ABSTRACT

Pipette tip made from plastics with an elongate, tubular body which comprises at a lower end a pipetting aperture, at an upper end a placement aperture (6) for placement on a receiving shank of a pipetting device, in the vicinity of the upper end a circumferential rib along a closed curve comprising different spacings from the lower end in different contour positions, a circumferential contact region on a surface of revolution on the inner face of the circumferential rib and at least one further rib extended from at least one position of the circumferential rib at a maximum distance from the lower end as far as the upper end.

16 Claims, 4 Drawing Sheets

PIPETTE TIP

CROSS-REFERENCE TO RELATED APPLICATIONS

Figure 1A:
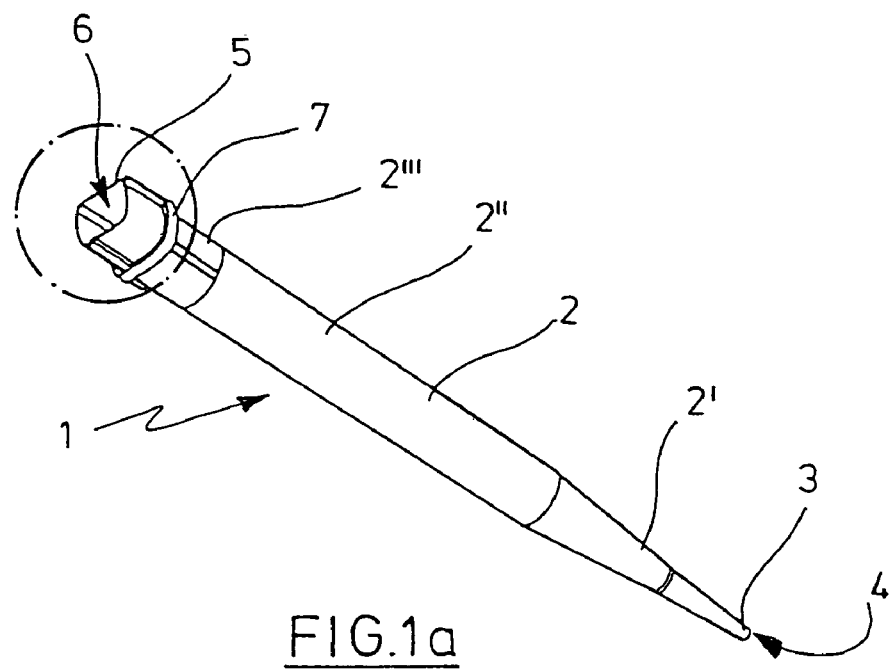
Figure 1B:
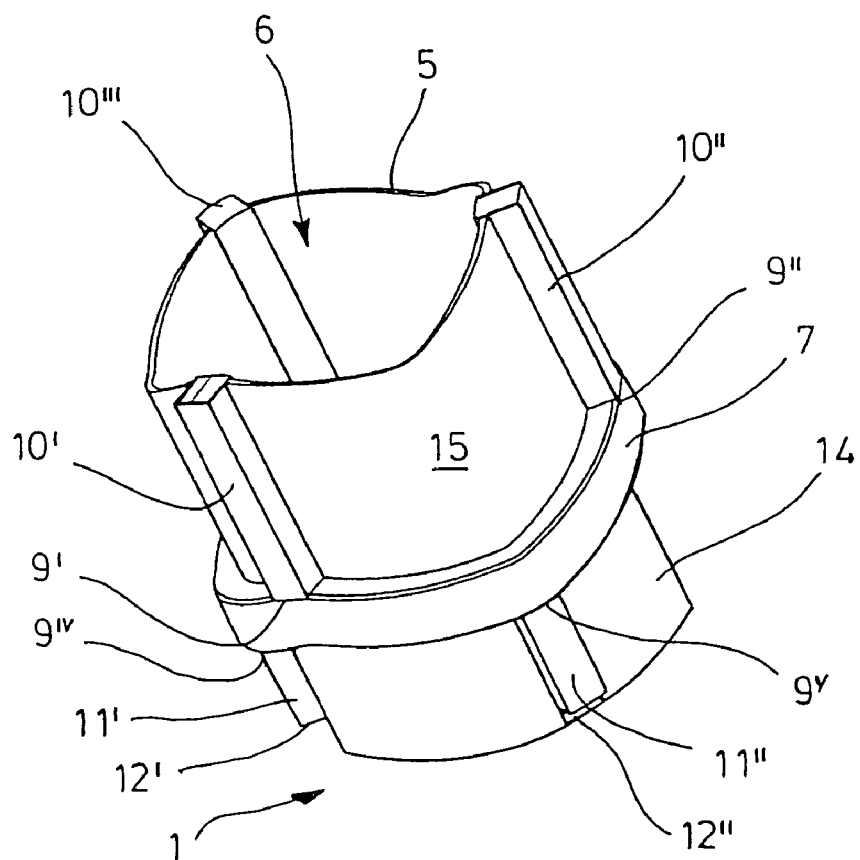

Not applicable.

STATEMENT REGARDING FEDERALLY SPONSORED RESEARCH

Not applicable.

BACKGROUND OF THE INVENTION

Pipette tips are used together with pipetting devices for metering liquids. Pipette tips have an elongate, tubular body which has a pipetting aperture at the lower end and a placement aperture at the upper end for placement on a receiving shank of the pipetting device. The receiving shank is typically of conical shape. However cylindrical receiving shanks or a mixture of forms are also known. Furthermore there are conical or cylindrical receiving shanks which have circumferential bulges or the like to intensify the sealing or clamping action. The pipetting device comprises a gas displacement device, which typically is designed as a piston-and-cylinder unit. The gas displacement device is connected to a through-aperture of the receiving shank. The pipette tip is fixed by forcing the receiving shank of the pipetting device into the placement aperture of the pipette tip on the pipetting device.

By means of the gas displacement device a gas column is displaced to draw liquid into the pipette tip placed on the receiving shank or to expel it from the tip. The gas column is typically an air column. When the gas column is displaced away from the pipette tip, a certain volume of liquid is drawn into the tubular body through the pipetting aperture. By displacing the gas column toward the pipette tip a volume of liquid is dispensed from the tubular body through the pipetting aperture.

There are pipetting devices in which the pipette tip is lifted off manually from the receiving shank. Typical pipetting devices have a throw-off device which acts on the upper edge of the pipette tip to force it off from the receiving shank.

The pipetting device can be a hand-operated pipette or a metering station, the gas displacement device able to be actuated by hand or driven by a motor. The placement and throw-off of the pipette tip can also be manual or driven by a motor.

To avoid faulty pipetting the pipette tip has to be sealingly fixed to the receiving shank. Moreover the forces for placement of the pipette tip on the receiving shank and throwing it off therefrom should not be too large. The contact region between the pipette tip and the receiving shank is of annular form. In the annular contact region the pipette tip is relatively rigid. As a result, the forces for placement and throwing off are already much too large. When thrown off the contact region overall passes simultaneously from cohesive friction to sliding friction. As a result much greater forces have to be applied for throwing off.

Starting therefrom the object of the invention is to produce a pipette tip in which the throw-off forces to release it from a receiving shank are reduced and which has an increased flexibility in the head region.

The object is achieved by a pipette tip with the features of claim 1. Advantageous embodiments of the pipette tip are indicated in the sub claims.

BREIF SUMMARY OF THE INVENTION

The pipette tip according to the invention made from plastics has an elongate, tubular body which comprises at a lower end a pipetting aperture, at an upper end a placement aperture for placement on a receiving shank of a pipetting device, in the vicinity of the upper end a circumferential rib along a closed curve, comprising different spacings from the lower end in different contour positions, a circumferential contact region on a surface of revolution on the inner face of the circumferential rib and at least one further rib extended from at least one position of the circumferential rib at a maximum distance from the lower end as far as the upper end.

The pipette tip according to the invention comes with the circumferential contact region on a surface of revolution on the inner face of the circumferential rib into sealing contact with the receiving shank of a pipetting device. The surface of revolution is constructed either on the inner face of the rib or is an intended surface of revolution which coincides in the contact region with the inner face of the rib. It is for example conical or cylindrical. The receiving shank comprises a correspondingly constructed further contact region which comes into sealing contact with the contact region.

When thrown off, the throw-off device of the pipetting device presses at the upper end of the pipette tip against the at least one further rib. By the at least one further rib the throw-off force is transmitted to at least one position of the circumferential rib at a maximum distance from the lower end. As a result this at least one position of the circumferential rib is pressed slightly toward the lower end. Relative to a plane positioned at right angles to the tubular body of the pipette tip, the circumferential rib is pressed slightly flatter. The at least one further rib forms a rigid region which when forces are transmitted is subjected to only relatively small deformations. As the circumferential rib is positioned transversely to the at least one further rib, it is relatively easily deformable by the forces introduced in the direction of the further rib. As a result the circumferential rib flares slightly and the static friction between the inner face of the circumferential rib or the contact region and the receiving shank is correspondingly reduced. Thus the throw-off forces required to release the pipette tip from the receiving shank are reduced. Moreover the pipette tip is more flexible in the region of the circumferential rib, so that the forces for placement on a receiving shank are also reduced and placement on receiving shanks of different dimensions is facilitated.

The curve along which the circumferential rib extends can have different geometries. According to an embodiment the circumferential rib has a path corresponding to a sine curve or a rectangular curve or a triangular curve or a sawtooth curve or a further periodic curve. The rectangular curve, triangular curve or sawtooth curve or other curves comprising principal corners can also be rounded off at the corners. The circumferential rib extends over one or more periods on the periphery. When extended over a plurality of periods the circumferential rib comprises a plurality of positions at a maximum distance from the lower end, in which the throw-off force can be introduced symmetrically into the circumferential rib via a plurality of further ribs. As a result the throw-off force is particularly advantageously reduced and the flexibility increased.

According to an embodiment the contact region has a circular path or a path corresponding to the path of the circumferential rib. Thus the contact region has for example the path of a sine curve or a rectangular curve or a triangular curve or a sawtooth curve or another periodic curve. As a result of the arrangement of the contact region on a surface of revolution the pipette tip can always be arranged in the desired rotational position on a receiving shank.

In principle the entire inner face of the circumferential rib can be the contact region. According to an embodiment the contact region is linear or strip-shaped, to attain high compression in the contact region. The strip-shaped contact region can extend over the entire height of the circumferential rib (seen in the axial direction of the pipette tip) or only over a part thereof.

According to an embodiment the circumferential rib and/or the at least one further rib protrudes outwardly and/or inwardly from the body.

According to an embodiment the inner face of the circumferential rib is conical or cylindrical. The conical or cylindrical form is in particular suited for placement on a conical or cylindrical receiving shank. The surface of revolution, on which the contact region extends, is preferably also conical or cylindrical.

According to an embodiment at least one further rib is positioned parallel to the axis of the tubular body and/or inclined thereto.

The upper end of the pipette tip can be designed in varying forms. According to an embodiment the upper end is planar or has a path parallel to the circumferential rib. In the latter case the upper end also has at least one position at a maximum distance from the lower end, via which throw-off forces can be specifically introduced.

According to an embodiment which is conducive to the introduction of throw-off forces in the at least one further rib, the at least one further rib is connected at the upper end to a further circumferential rib. This can form a planar upper end or an upper end of the pipette tip parallel to the circumferential rib.

According to an embodiment further ribs inclined toward the axis of the tubular body are connected to one another at positions of the circumferential rib at a maximum distance from the lower end and at positions arranged at the upper end. The throw-off forces are introduced into the further ribs via the connection points at the upper end and transmitted therefrom to the positions of the circumferential rib at a maximum distance from the lower end. As a result of the inclination of the further ribs the throw-off forces are transmitted as in a toggle mechanism, so that particularly large forces can be introduced into the circumferential rib.

According to an embodiment the inclined further ribs are connected to one another on a further circumferential rib. Thus the inclined further ribs simultaneously form the upper end of the pipette tip.

According to an embodiment, in a flexible axial region adjacent to the circumferential rib on the face facing the lower end the body has a smaller wall thickness and/or a softer material than in a region closer to the lower end. The flexible axial region facilitates the deformation of the circumferential rib by the throw-off forces introduced via the at least one further rib and the flexibility in the sealing region.

According to an embodiment, between the circumferential rib and the at least one further rib and optionally the further circumferential rib the body has no wall or a smaller wall thickness and/or a softer material than between the lower end and the circumferential rib or the flexible axial region. As a result the force transmission from the upper end is facilitated via the at least one further rib and the throwing-off facilitated and the flexibility improved.

To support the circumferential rib over the flexible axial region and/or to improve the ejection in the injection mould, according to an embodiment the pipette tip comprises further ribs which are oriented from positions of the circumferential rib at the smallest distance from the lower end toward the lower end. Preferably these ribs extend substantially over the more flexible axial region.

Finally, according to an embodiment the pipette tip is manufactured integrally from at least one plastic material. The pipette tip can advantageously be manufactured from a single plastic material, the flexibility in the upper region being improved by wall thickening/thinning or perforations. Furthermore the pipette tip can advantageously be manufactured by multi component injection moulding from a plurality of different plastics of varying rigidity or softness.

The pipette tip will be described in more detail below with reference to the accompanying drawings of embodiments in which:

DETAILED DESCRIPTION OF THE INVENTION

Figure 1D:
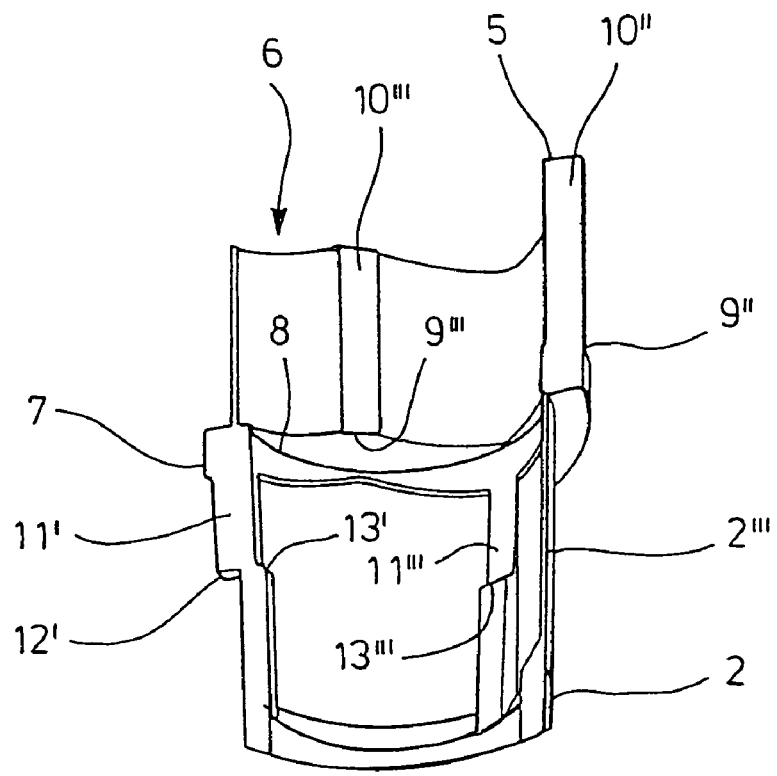
Figure 1C:
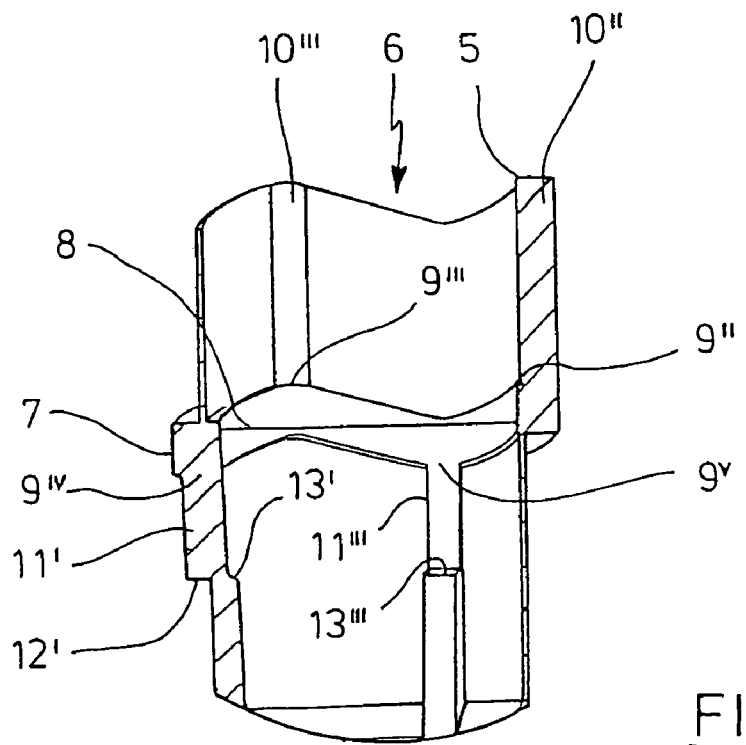
Figure 2A:
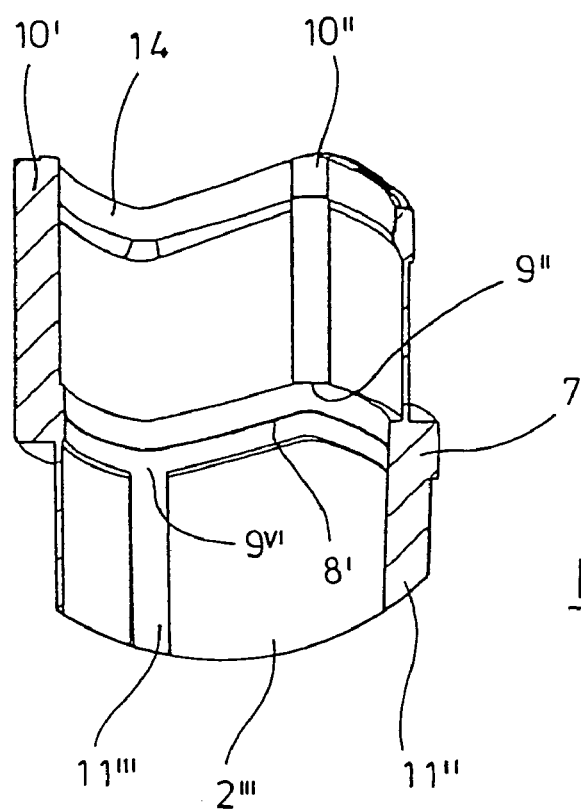
Figure 2B:
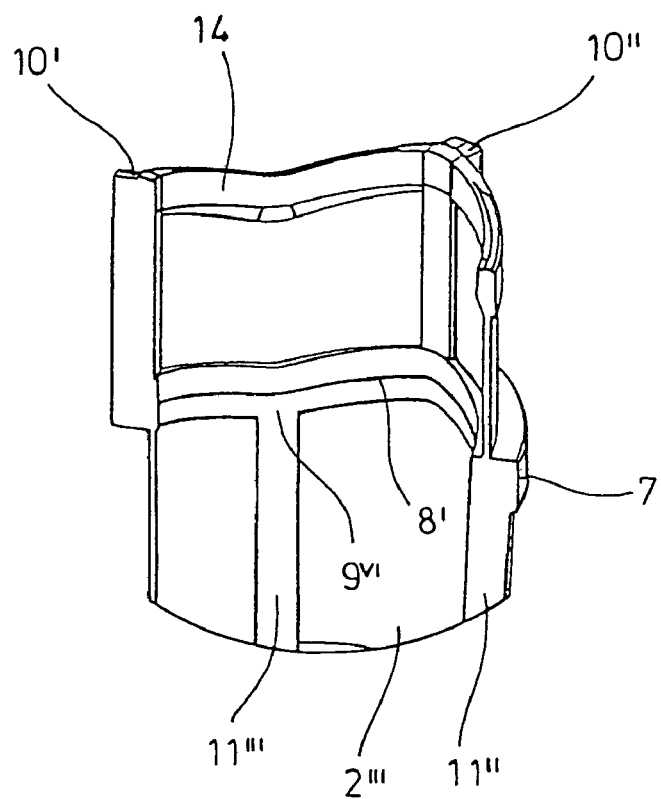
Figure 3A:
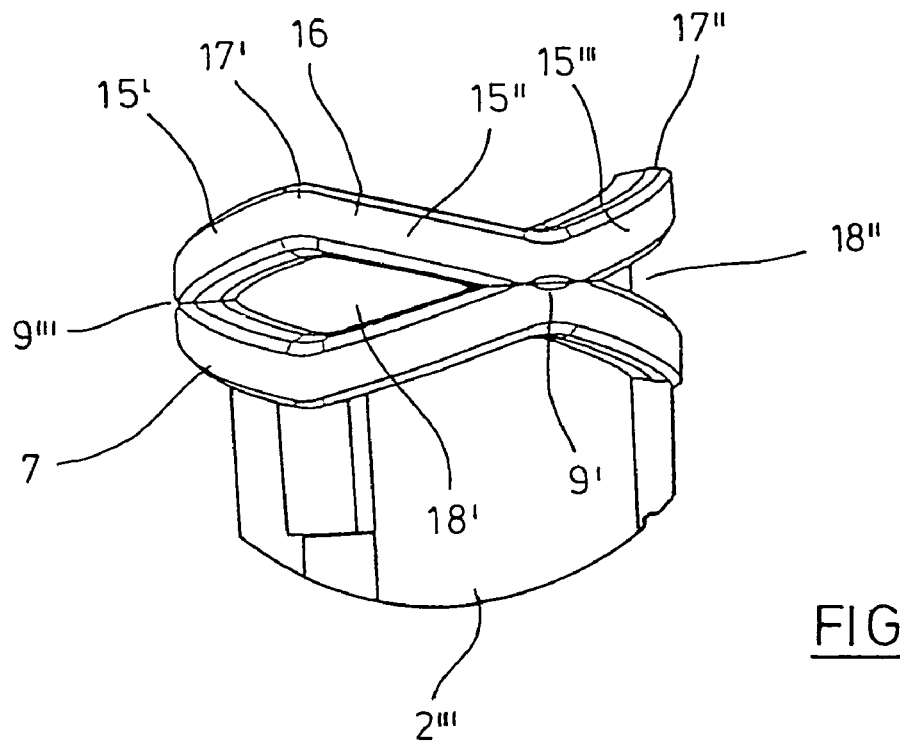
Figure 3B:
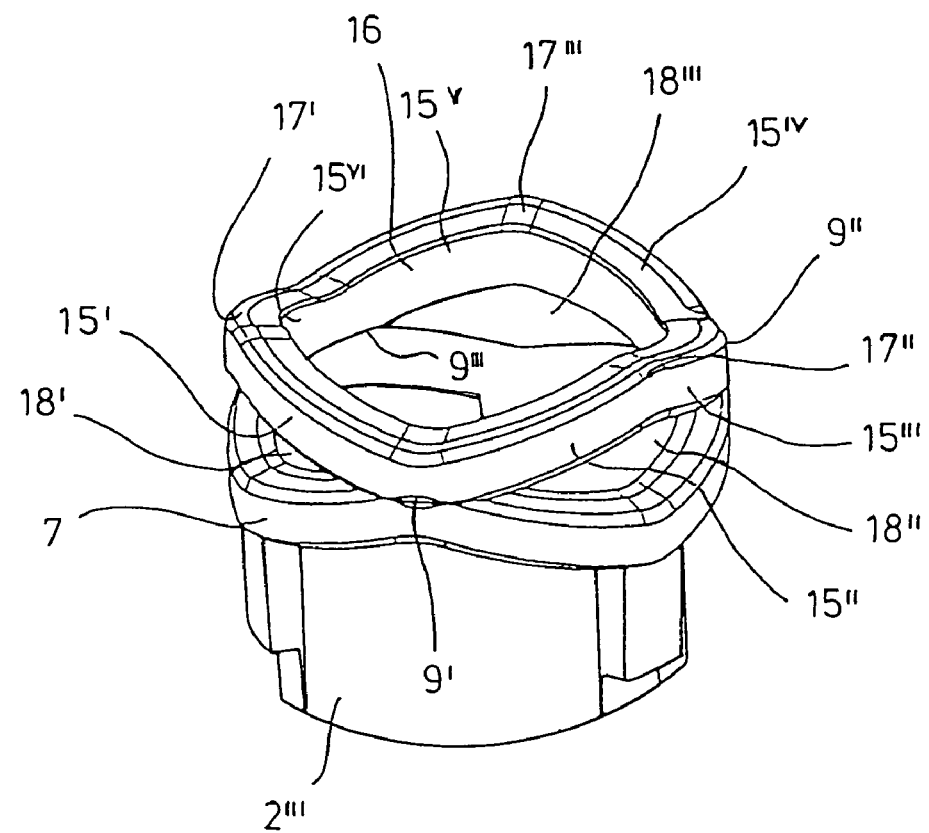

While this invention may be embodied in many different forms, there are described in detail herein a specific preferred embodiment of the invention. This description is an exemplification of the principles of the invention and is not intended to limit the invention to the particular embodiment illustrated FIGS. 1a to d show a pipette tip with wave-shaped circumferential rib and further ribs parallel to the axis in a perspective side view (FIG. 1a), in an enlarged detail of the upper end from the same perspective (FIG. 1b), in an enlarged longitudinal section through the upper end (FIG. 1c) and in the same section in a further perspective (FIG. 1d);

FIGS. 2a and b show a pipette tip with a further circumferential rib at the upper end in a longitudinal section through the upper end (FIG. 2a) and in the same longitudinal section in a further perspective (FIG. 2b);

FIGS. 3a and b show a pipette tip with further ribs oriented obliquely and connected to one another on a further circumferential rib in an enlarged side view of the upper end (FIG. 3a) and in an angled perspective view from above of the upper end (FIG. 3b).

In the following description of different embodiments similar features are designated by the same reference numerals.

According to FIG. 1 a pipette tip 1 has an elongate, tubular body 2 which in the example substantially comprises a conical first section 2', a cylindrical main section 2" and a head section 2''' described below in more detail.

At a lower end 3 the tubular body 2 has a pipetting aperture 4 and at an upper end 5 a placement aperture 6 for placement on the receiving shank of a pipetting device.

The lower end 3 of the pipette tip owes its designation to the fact that during use it is regularly arranged below, whilst the designation of the upper end 5 is based on the fact that during use it is regularly located above.

At a distance from the upper end 5 the head section 2''' has a circumferential rib 7 along a closed curve. The rib 7 slightly protrudes from the outer face and the inner face of the body 2. In cross-section it is of approximately rectangular shape. It has a wave-shaped path, ie it extends in a wave-shape or sine-shape relative to a plane extending perpendicular to the longitudinal axis of the pipette tip. In the example the rib 7 extends over three periods of a sine function.

At the inner contour of the rib 7 a circular contact region (8) is present which is of linear construction.

The upper end 5 has a path which is parallel to the path of the circumferential rib 7.

Starting from the three maxima 9', 9'', 9''' of the circumferential rib 7, ie the positions of the circumferential rib 7 at a maximum distance from the lower end 3, three further ribs extend 10', 10'', 10''' parallel to the longitudinal axis of the tubular body 2 as far as the upper end 5. The further ribs 10', 10'', 10''' also protrude slightly from the inner and the outer face of the body 2 and have an approximately rectangular cross-section.

Furthermore the body comprises further axially extending ribs 11', 11'', 11''' which come from the three minima $9^{IV}, 9^{V}, 9^{VI}$ of the circumferential rib 7, ie from the positions of the circumferential rib 7 which are closest to the lower end 3. These ribs 11', 11'', 11''' extend over the lower part of the head region 2''' as far as the main section 2' and protrude over the two sides of the body 2. They also have an approximately rectangular cross-section. Outside they are defined below by a step 12', 12'', 12''' and inside they comprise a step 13', 13'', 13'''. The steps 12', 12'', 12''' serve to support it on the edges of the holes of a holding device ("rack") and the steps 13', 13'', 13''' to restrict the placement on a receiving shank.

In the head section 2''' on the two faces of the circumferential rib 7 between the ribs 10', 10'', 10''' and 11', 11'' and 11''' the body 2 has a wall thickness which is reduced relative to the main section 2'.

When attaching a pipetting device to a receiving shank the circular contact region 8 ensures a sealed and tight fit. When a throw-off device is pressed against the upper ends of the further ribs 10' to 10''', the circumferential rib 7 is downwardly pressed thereby at the maxima 9' to 9'''. Thus the circumferential rib 7 is supported by the ribs 11' to 11''' at the minima $9^{IV}, 9^{V}, 9^{VI}$. As a result the inner face of the circumferential rib 7 and thus the contact region 8 is flared, whereby the throw-off forces required for throwing-off are reduced. By the reduced wall thickness in the head region 2''', the disclosed deformations are facilitated. Moreover by the increased flexibility in the head region 2''' which reduces the force required to push onto a receiving shank, pushing onto receiving shanks with different dimensions is facilitated.

The embodiment in FIG. 2 differs from the one previously disclosed, in particular in that at the upper end 5 a further circumferential rib 14 is present. As a result the force introduction into the upper end of the ribs 10' to 10''' is improved. Moreover the path of the contact region 8' follows the sine shaped path of the circumferential rib 7. The contact region 8' is arranged on a conical surface of revolution. For example the entire inner face of the rib 7 is conical.

The embodiment of FIG. 3 differs from those previously disclosed, in that instead of further ribs 10' to 10''' oriented parallel to the longitudinal axis of the body 2, further ribs 15' to $15^{VI}$ inclined toward the longitudinal axis of the body 2 are present. These are respectively connected at one end to a maximum 9' to 9''' and at their other end respectively to an adjacent further rib 15' to $15^{VI}$, so that they form as a whole a further circumferential rib 16.

At the last-mentioned connection points 17' to 17''' the inclined further ribs 15' to $15^{VI}$ are at the furthest distance from the lower end 3. A throw-off device can be attached there which via the inclined further ribs 15' to $15^{VI}$ downwardly presses the maxima 9' to 9''' and effects the flaring on the inner contour of the circumferential rib 7. This embodiment has free spaces 18', 18'', 18''' between the circumferential rib 7 and the inclined ribs 15' to $15^{VI}$ which additionally increase the flexibility in the head region 2'''. On the other face of the circumferential rib 7 the wall thickness of the head portion 2''' is reduced.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

What is claimed is:

1. Pipette tip made from plastics with an elongate, tubular body (2) which comprises at a lower end (3) a pipetting aperture (4), at an upper end (5) a placement aperture (6) for placement on a receiving shank of a pipetting device, in the vicinity of the upper end (5) a circumferential rib (7) along a closed curve, comprising different spacings from the lower end in different contour positions, a circumferential contact region (8) on a surface of revolution on the inner face of the circumferential rib (7) and at least one further rib (10', 10'', 10''') extended from at least one position (9', 9'', 9''') of the circumferential rib (7) at a maximum distance from the lower end as far as the upper end (5).

2. Pipette tip according to claim 1, in which the circumferential rib (7) has a path corresponding to a sine curve or a rectangular curve or a triangular curve or a sawtooth curve or a further periodic curve.

3. Pipette tip according to claim 1, in which the contact region (8) has a circular path or a path corresponding to the path of the circumferential rib (7).

4. Pipette tip according to claim 1, in which the contact region (8) is linear or strip-shaped.

5. Pipette tip according to claim 1, in which the circumferential rib (7) and/or the at least one further rib (10', 10'', 10''') protrudes outwardly and/or inwardly from the body (2).

6. Pipette tip according to claim 1, in which the inner face of the circumferential rib (7) is conical or cylindrical.

7. Pipette tip according to claim 1, in which the at least further rib (10', 10'', 10''') is positioned parallel to the axis of the tubular body (2) and/or inclined thereto.

8. Pipette tip according to claim 1, whose upper end (5) is planar or has a path parallel to the circumferential rib (7).

9. Pipette tip according to claim 1, in which the at least one further rib (10', 10'', 10''') is connected at the upper end (5) to a further circumferential rib (14).

10. Pipette tip according to claim 1, in which the further ribs (15' to 15VI) inclined toward the axis of the tubular body (2) are connected to one another at positions (9', 9", 9''') of the circumferential rib (7) at a maximum distance from the lower end and at positions arranged at the upper end (5).

11. Pipette tip according to claim 10, in which the inclined further ribs (15' to 15VI) are connected to one another on a further circumferential rib (16).

12. Pipette tip according to claim 1, whose body (2) in a flexible axial region (2''') adjacent to the circumferential rib (7) on the face facing the lower end (3) has a smaller wall thickness and/or a softer material than in a region (2) closer to the lower end (3).

13. Pipette tip according to claim 1, whose body (2) between the circumferential rib (7) and the at least one further rib (10' to 10''') and optionally the further circumferential rib (14) has no wall or a smaller wall thickness and/or a softer material than between the lower end (3) and the circumferential rib (7) or the flexible axial region (2''').

14. Pipette tip according to claim 1, which comprises further ribs (11' to 11'''), which are oriented from positions (9IV, 9V, 9VI) of the circumferential rib (7) at the smallest distance from the lower end (3) toward the lower end (3).

15. Pipette tip according to claim 1, which is manufactured integrally from at least one plastic material.

16. A pipette tip made from plastics, comprising:
an elongate tubular body having upper and lower ends;
the lower end having a pipetting aperture;
the upper end having a placement aperture for placement on a receiving shank of a pipetting device;
a circumferential rib extending along a closed curve, near the upper end of the elongate tubular body, having different spacings from the lower end in different contour positions;
a circumferential contact region on a surface of revolution on the inner face of the circumferential rib;
at least one further rib extended from at least one position of the circumferential rib at a maximum distance from the lower end as far as the upper end, and
the circumferential rib flares slightly when a throw-off force is applied at the upper end of the elongate tubular body against the at least one further rib.

* * * * *